US00PP34456P3

(12) United States Plant Patent
Noordhuis et al.

(10) Patent No.: US PP34,456 P3
(45) Date of Patent: Jul. 26, 2022

(54) ***HELLEBORUS* PLANT NAMED 'ET EPB 1717'**

(50) Latin Name: ***Helleborus orientalis* X *Helleborus ericsmithii***
Varietal Denomination: 'ET EPB 1717'

(71) Applicants: Bart Noordhuis, Boijl (NL); Elisabeth Bisschop, Boijl (NL)

(72) Inventors: Bart Noordhuis, Boijl (NL); Elisabeth Bisschop, Boijl (NL)

(73) Assignee: ETERNAL PLANT BOIJL B.V., Boijl (NL)

( * ) Notice: Subject to any disclaimer, the term of this patent is extended or adjusted under 35 U.S.C. 154(b) by 0 days.

(21) Appl. No.: 17/530,405

(22) Filed: Nov. 18, 2021

(65) Prior Publication Data

US 2022/0167541 P1 May 26, 2022

(30) Foreign Application Priority Data

Nov. 20, 2020 (QZ) ..... PBR 2020/2951

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
CPC ... A01H 5/02; A01H 5/00; A01H 6/72; A01H 1/107; A01H 1/121; A01H 1/1215
See application file for complete search history.

*Primary Examiner* — June Hwu
(74) *Attorney, Agent, or Firm* — C. Anne Whealy

(57) ABSTRACT

A new and distinct cultivar of *Helleborus* plant named 'ET EPB 1717', characterized by its upright plant habit; moderately vigorous to vigorous growth habit; continuous and freely flowering habit; relatively large purplish red-colored flowers that are held above the foliar plane on relatively long peduncles; and good garden performance.

2 Drawing Sheets

Figure 1:
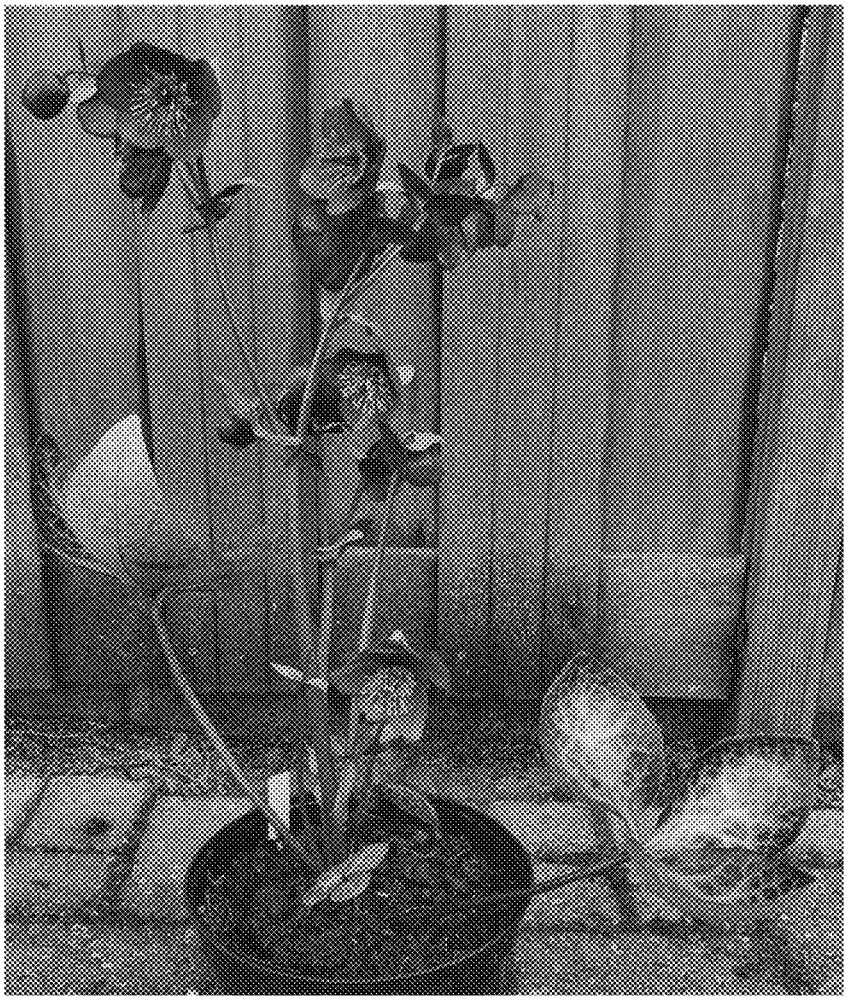

Botanical designation: *Helleborus orientalis* X *Helleborus ericsmithii.*

Cultivar denomination: 'ET EPB 1717'.

STATEMENT REGARDING PRIOR DISCLOSURES BY INVENTOR & APPLICANT/ASSIGNEE

An European Community Plant Breeder's Rights application for the instant plant was filed by the Assignee, Eternal Plant Boijl B.V. of Boijl, The Netherlands on Nov. 20, 2020, application number 2020/2951. Foreign priority is claimed to this application.

The Inventors/Applicants and Assignee assert that no publications nor advertisements relating to sales, offers for sale or public distribution occurred more than one year prior to the effective filing date of this application. Any information about the claimed plant would have been obtained from a direct or indirect disclosure from the Inventors/Applicants and/or Assignee. Inventors/Applicants and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus orientalis* X *Helleborus ericsmithii* and hereinafter referred to by the name 'ET EPB 1717'.

The new *Helleborus* plant is a product of a planned breeding program conducted by the Inventors in Boijl, The Netherlands. The objective of the breeding program was to create new freely-flowering *Helleborus* plants with strong peduncles that hold numerous attractive flowers above the foliar plane.

The new *Helleborus* plant originated from a cross-pollination conducted by the Inventors in Boijl, The Netherlans in February, 2015 of a proprietary selection of *Helleborus orientalis* identified as code number 718, as the female, or seed, parent, not patented, with a proprietary selection of *Helleborus ericsmithii* identified as code number 1204, as the male, or pollen, parent, not patented. The new *Helleborus* plant was discovered and selected by the Inventors as a single flowering plant from within the progeny of the stated cross-pollination grown in a controlled greenhouse environment in Boijl, The Netherlands in February, 2017.

Asexual reproduction of the new *Helleborus* plant by meristem culture in a controlled greenhouse environment in Boijl, The Netherlands since May, 2018, has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype of the new *Helleborus* plant may vary somewhat with variations in environmental conditions such as temperature and light intensity without, however, any variance in genotype of the new *Helleborus* plant.

The following traits have been repeatedly observed and are determined to be the unique characteristics of 'ET EPB 1717'. These characteristics in combination distinguish 'ET EPB 1717' as a new and distinct *Helleborus* plant:

1. Upright plant habit.
2. Moderately vigorous to vigorous growth habit.
3. Continuous and freely flowering habit.
4. Relatively large purplish red-colored flowers that are held above the foliar plane on relatively long peduncles.
5. Good garden performance.

Plants of the new *Helleborus* differ from plants of the female parent selection in the following characteristics:

1. Plants of the new *Helleborus* are more compact than plants of the female parent selection.
2. Flowers of plants of the new *Helleborus* are lighter in color than flowers of plants of the female parent selection.

Plants of the new *Helleborus* differ from plants of the male parent selection in the following characteristics:

1. Plants of the new *Helleborus* are taller than plants of the male parent selection.
2. Plants of the new *Helleborus* have slightly larger flowers than plants of the male parent selection.
3. Plants of the new *Helleborus* and the male parent selection differ in flower color as plants of the new *Helleborus* have purplish red-colored flowers whereas plants of the male parent selection have more purple-colored flowers.

Plants of the new *Helleborus* can be compared to plants of *Helleborus* x *hybridus* 'ABCRD02', disclosed in U.S. Plant Pat. No. 24,720. In side-by-side comparisons, plants of the new *Helleborus* differ from plants of 'ABCRD02' in the following characteristics:

1. Plants of the new *Helleborus* are taller than plants of 'ABCRD02'.
2. Stems of plants of the new *Helleborus* are reddish green in color than stems of plants of 'ABCRD02' which are green in color.
3. Plants of the new *Helleborus* have smaller leaves than plants of 'ABCRD02'.
4. Plants of the new *Helleborus* are more freely flowering than plants of 'ABCRD02'.
5. Flowers of plants of the new *Helleborus* are darker purplish red in color than flowers of plants of 'ABCRD02'.

Plants of the new *Helleborus* can also be compared to plants of *Helleborus* x *hybridus* 'EPB 210', disclosed in U.S. Plant Pat. No. 29,873. In side-by-side comparisons, plants of the new *Helleborus* differ from plants of 'EPB 210' in the following characteristics:

1. Plants of the new *Helleborus* are taller than plants of 'EPB 210'.
2. Flowers of plants of the new *Helleborus* are darker in color than flowers of plants of 'EPB 210'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a side perspective view of a typical flowering plant of 'ET EPB 1717' grown in a container.

Figure 2:
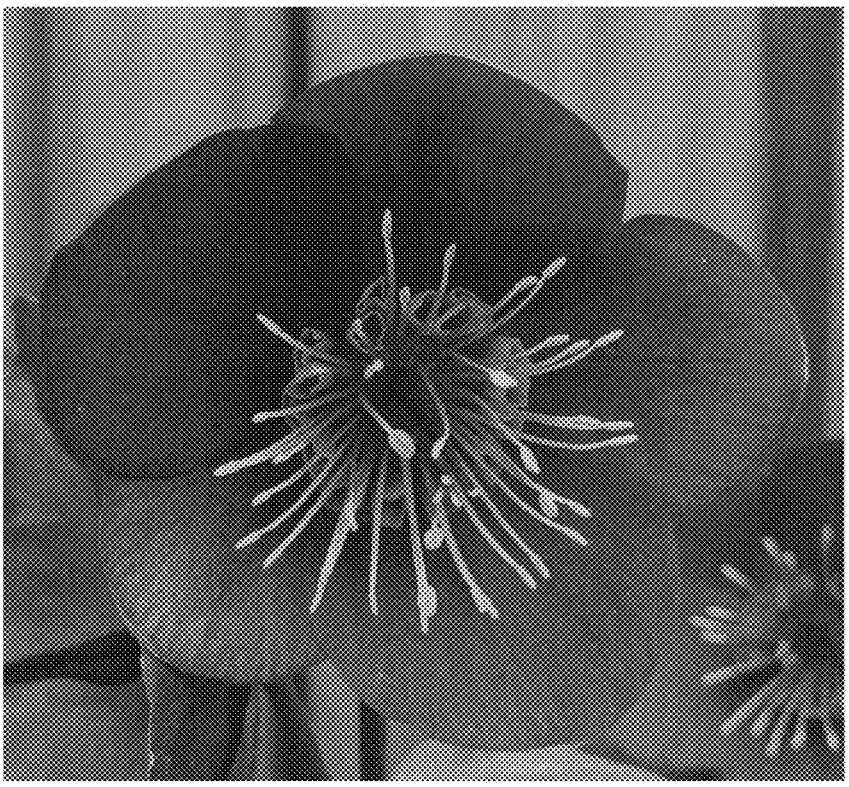

The photograph on the second sheet (FIG. 2) is a close-up view of a typical flower of 'ET EPB 1717'.

DETAILED BOTANICAL DESCRIPTION

The aforementioned photographs and following observations, measurements and values describe plants grown during the winter in three-liter containers in an outdoor nursery in Boijl, The Netherlands and under cultural practices typical of commercial *Helleborus* production. During the production of the plants, day temperatures ranged from 0° C. to 10° C. and night temperatures ranged from −15° C. to 0° C. Plants were one year old when the photographs and the description were taken. In the following description, color references are made to The Royal Horticultural Society Colour Chart, 2001 Edition, except where general terms of ordinary dictionary significance are used.

Botanical classification: *Helleborus hybridus* 'ET EPB 1717'.

Parentage:

*Female, or seed, parent.*—Proprietary selection of *Helleborus orientalis* identified as code number 718, not patented.

*Male, or pollen, parent.*—Proprietary selection of *Helleborus ericsmithii* identified as code number 1204, not patented.

Propagation:

*Type.*—By meristem culture.

*Time to initiate roots, summer.*—About 15 days at temperatures about 22° C. to 25° C.

*Time to initiate roots, winter.*—About 15 to 22 days at temperatures about 5° C. to 10° C.

*Time to produce a rooted young plant, summer.*—About two months at temperatures about 20° C.

*Time to produce a rooted young plant, winter.*—About 55 to 60 days at temperatures about 12° C. to 15° C.

*Root description.*—Fleshy, vigorous; typically white to brown in color, actual color of the roots is dependent on substrate composition, water quality, fertilizer type and formulation, substrate temperature and physiological age of roots.

*Rooting habit.*—Freely branching; moderately dense.

Plant description:

*Plant and growth habit.*—Herbaceous perennial; upright plant habit with flowers held above the foliar plane; moderately vigorous to vigorous growth habit and moderate growth rate.

*Plant height.*—About 50 cm to 55 cm.

*Plant diameter* (*area of spread*).—About 20 cm to 25 cm.

*Stems.*—Strength: Strong. Aspect: Mostly upright. Texture and luster: Smooth, glabrous; glossy. Color: Close to 146B densely covered with spots, close to 187B.

Leaf description:

*Arrangement.*—Leaves arranged alternately in a basal rosette; leaves palmately compound with three to five leaflets per leaf.

*Leaflet length.*—About 10 cm to 15 cm.

*Leaflet width.*—About 8 cm to 10 cm.

*Leaflet shape.*—Ovate to obovate.

*Leaflet apex.*—Acute.

*Leaflet base.*—Acute.

*Leaflet margin.*—Serrate.

*Leaflet texture and luster, upper surface.*—Smooth, glabrous; leathery; glossy.

*Leaflet texture and luster, lower surface.*—Smooth, glabrous; leathery; somewhat glossy.

*Leaflet venation pattern.*—Pinnate.

*Leaflet color.*—Developing leaves, upper surface: Close to 137A; center, marbled with close to 139D. Developing leaves, lower surface: Close to 148B slightly overlain with close to 187A. Fully expanded leaves, upper surface: Close to 139A; center, marbled with close to 139C to 139D; venation, close to 139C to 139D. Fully expanded leaves, lower surface: Close to 147B; venation, close to 147B tinged with 187A.

*Petioles.*—Length, fully expanded leaves: About 15 cm to 20 cm. Diameter, fully expanded leaves: About 4 mm to 7 mm. Texture, upper and lower surfaces: Smooth, glabrous. Color, upper and lower surfaces: Close to 146B; densely covered with spots, close to 187A.

Flower description:

*Flower shape and habit.*—Single rotate flowers arranged in loosely branched cymes; freely flowering habit with typically about 10 to 20 flowers developing per cyme and up to 40 flowers developing per cyme in the second year of growth; flowers facing outwardly to somewhat drooping.

*Fragrance.*—None detected.

*Natural flowering season.*—Plants begin flowering about two months after planting; plants flower from January until March in The Netherlands.

*Flower longevity on the plant.*—About three months; flowers persistent.

*Inflorescence height.*—About 45 cm to 55 cm.

*Inflorescence diameter.*—About 25 cm to 35 cm.

*Flower buds.*—Length: About 1 cm to 3 cm. Diameter: About 1 cm to 2 cm. Shape: Ovoid. Color: Close to N77A.

*Flower diameter.*—About 6 cm to 8 cm.

*Flower depth (height).*—About 1 cm to 3 cm.

*Petals.*—None observed; transformed into nectaries.

*Sepals.*—Quantity and arrangement: Five arranged in a single whorl. Length: About 3 cm to 4 cm. Width: About 3.5 cm to 4 cm. Shape: Ovate to obovate. Apex: Obtuse and occasionally emarginate. Base: Rounded. Margin: Mostly entire and occasionally emarginate. Texture and luster, upper and lower surfaces: Smooth, glabrous; matte. Color: When opening and fully opened, upper surface: Close to N79B; color does not change with subsequent development. When opening and fully opened, lower surface: Close to N77A; color does not change with subsequent development.

*Peduncles.*—Length: About 15 cm to 25 cm. Diameter: About 5 mm to 10 mm. Strength: Strong. Aspect: Mostly upright. Texture: Smooth, glabrous. Color: Close to 146B heavily covered with spots, close to 187B.

*Pedicels.*—Length: About 6 cm to 12 cm. Diameter: About 4 mm. Aspect: About 10° from peduncle axis. Strength: Strong. Texture: Smooth, glabrous. Color: Close to 187A to 187B.

*Reproductive organs.*—Stamens: Quantity per flower: About 75. Filament length: About 2 cm. Filament color: Close to N79D. Anther shape: Ovate to oblong. Anther length: About 3 mm. Anther color: Close to 4B. Pollen amount: Scarce. Pollen color: Close to 4B. Pistils: Quantity per flower: About five. Pistil length: About 2 cm. Stigma shape: Club-shaped. Stigma color: Close to 4D. Style length: About 2 cm. Style color: Close to N79A to N79B. Ovary color: Close to N79A to N79B.

*Nectaries.*—Quantity per flower: About 10 to 15. Length: About 5 mm to 8 mm. Width: About 3 mm to 5 mm. Shape: Funnelform. Color: Close to N144B.

*Seeds and fruits.*—To date, seed and fruit development have not been observed on plants of the new *Helleborus.*

Garden performance: Plants of the new *Helleborus* have been observed to have good garden performance and to tolerate rain, wind and temperatures ranging from about −10° C. to about 35° C.

Pathogen & pest resistance: To date, plants of the new *Helleborus* have not been observed to be resistant to pathogens and pests common to *Helleborus* plants.

It is claimed:

1. A new and distinct *Helleborus* plant named 'ET EPB 1717' as illustrated and described.

* * * * *